Figure 1:
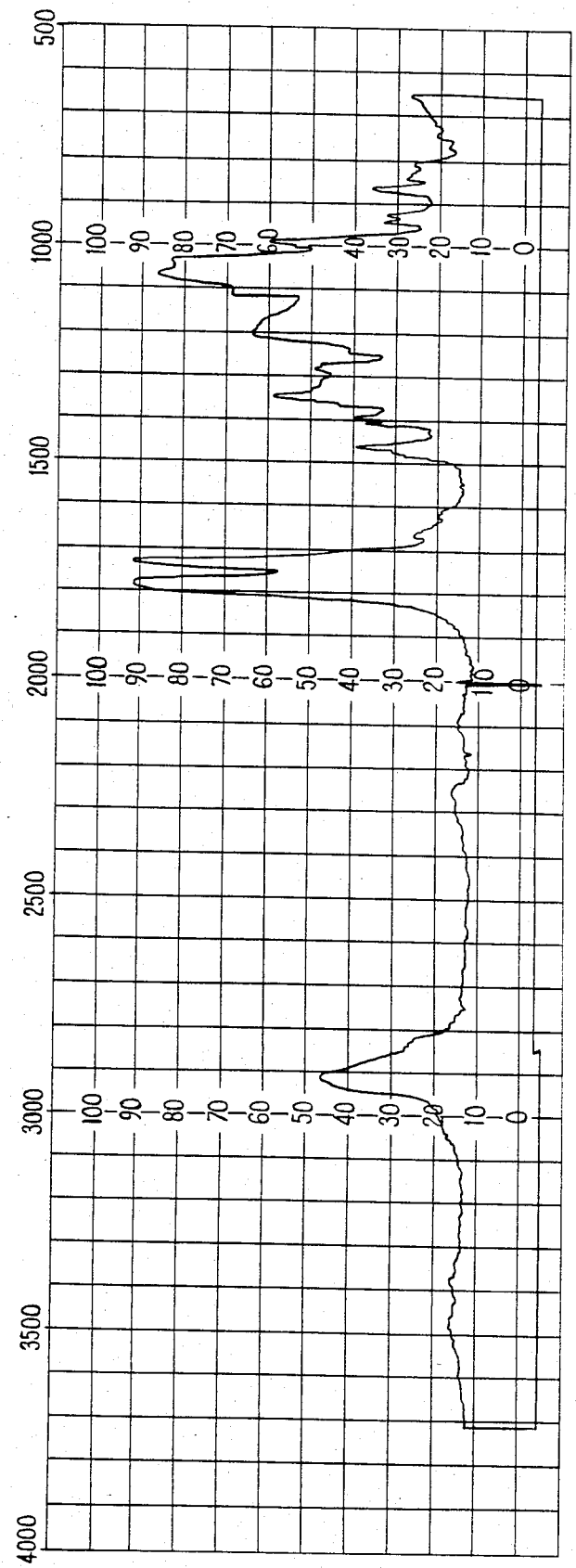

United States Patent [19]

Napier et al.

[11] Patent Number: 4,529,734

[45] Date of Patent: Jul. 16, 1985

[54] 2-FORMYLOXYMETHYL-CLAVAM

[75] Inventors: Eunice J. Napier, Mattingley; James K. Evans, High Wycombe; David Noble, Marlow; Michael Bushell, Nr. High Wycombe, all of England

[73] Assignee: Glaxo Laboratories Limited, London, England

[21] Appl. No.: 324,054

[22] Filed: Nov. 23, 1981

Related U.S. Application Data

[63] Continuation of Ser. No. 211,804, Dec. 1, 1980, abandoned, which is a continuation of Ser. No. 11,684, Feb. 12, 1979, abandoned, which is a continuation of Ser. No. 804,348, Jun. 7, 1977, abandoned.

[30] Foreign Application Priority Data

Jun. 8, 1976 [GB] United Kingdom ............... 23736/76

[51] Int. Cl.³ ..................... A61K 31/42; C07D 498/04

[52] U.S. Cl. ................... 514/375; 260/245.3; 435/119

[58] Field of Search ............. 260/245.3; 424/272

[56] References Cited

U.S. PATENT DOCUMENTS 4,093,626  6/1978  Hunt ................................ 260/245.3

FOREIGN PATENT DOCUMENTS 2702091  7/1977  Fed. Rep. of Germany .
1315177  4/1973  United Kingdom .

Primary Examiner—Mark L. Berch
Attorney, Agent, or Firm—Bacon & Thomas

[57] ABSTRACT

2-Formyloxymethyl-clavam is described and its use as an antifungal compound against a range of fungi for both medical and horticultural and agricultural use is disclosed. Processes for isolating the compound from fermentations of strains of *Streptomyces clavuligerus* are described.

13 Claims, 1 Drawing Figure

2-FORMYLOXYMETHYL-CLAVAM

This application is a continuation of application Ser. No. 211,804, filed 12/1/80, abandoned, which is a continuation of Ser. No. 011,684, filed 2/12/79 abandoned, which is a continuation of Ser. No. 804,348, filed 6/7/77, abandoned.

This invention relates to a novel antifungal compound and to a process for its production.

Fermentation of *Streptomyces clavuligerus* and in particular strain NRRL 3585, is known to produce a number of antibiotic substances and British Patent Specification 1,315,177 describes and claims the cultivation of *Streptomyces clavuligerus* strain NRRL 3585 until a substantial amount of two antibiotics, referred to as Antibiotics A 16886 I and A 16886 II is produced.

We have now been able to isolate from strains of *Streptomyces clavuligerus* a further compound which has been found to possess antifungal activity.

The compounds in this specification are named with reference to 'clavam', the name given to the parent heterocycle of formula A

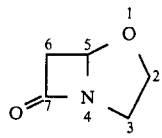

by analogy with the term 'cepham' used in the naming of cephalosporin compounds in J. Amer. Chem. Soc. 1962, 84.

According to one aspect of this invention, therefore, we provide 2-formyloxymethyl-clavam having the formula (I)

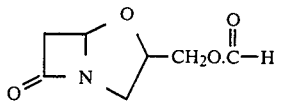

a deuterochloroform solution of which has $\tau$ values in the 100 MHz proton nmr spectrum shown in Table 1 herein.

It is believed that the $\tau$ values given in Table 1 are subject to an experimental error of 0.05.

TABLE 1

| $\tau$ values | $\tau$ values |
|---|---|
| 1.92 (s) (1H) | 4.68 (d, 2.5 Hz) (1H) |
| 5.43 (multiplet) (1H) | 5.76 (d, 4 Hz) (2H) |
| 6.00 (dd, 7 Hz, 11.5 Hz) (1H) | 7.20 (dd, 6 Hz, 11.5 Hz) (1H) |
| 6.70 (dd, 2.5 Hz, 16 Hz) (1H) | 7.19 (d, 16 Hz) (1H) |

It is to be noted that although the stereochemical configuration of the compound of the invention is not known, the stated $\tau$ values in Table 1 are characteristic of the particular configuration existing in the compound of formula (I).

The compound of the invention has been found to possess antifungal activity, for example against strains of *Candida albicans*, *Saccharomyces cerevisiae*, *Saccharomyces carlsbergensis*, *Trichophyton mentagrophytes*, *Epidermophyton flocossum* and *Microspora canis*.

Accordingly, we further provide an antifungal composition which includes the compound of formula I together with a suitable carrier or diluent.

According to a still further aspect of the invention, we provide a method of combatting fungi whereby an effective quantity of the compound of formula I is administered to a human or animal subject either prophylactically or therapeutically.

The compound of the inventiion has further been found to have activity against a range of fungal plant pathogens, for example *Botrytis allii* (onion neck rot), *Cercospora melanis* (melon blotch), *Verticillium* sp. (tomato wilt), *Fusarium graminium* (cereal seedling blight), *Rhizoctonia solani* (potato black scurf), *Alternaria brassicicola* (cabbage black spot), *Colletotricum coccodes* (tomato anthracnose), *Nectria galligena* (apple canker), *Botrytis cinerea* (grey rot), *Ashbya gossypii* (cotton boll disease), *Eremothecium ashbyi* (cotton boll disease), and *Fusarium oxysporum* (fusarium wilt), and some insect pathogens, for example *Beauvaria bassiana*.

The compound has also shown activity against *Erysiphe graminis* (barley mildew).

The compound according to the invention may be used in human and veterinary medicine in the form of pharmaceutical compositions containing one or more pharmaceutical carriers or excipients suitable, for example, for oral, topical, rectal, intravaginal or parenteral administration. Such compositions may be used together with other medicinal agents. The compositions may be formulated in conventional manner. Thus, for example formulations for external applications may be prepared in oily, aqueous or powdered media in the form of conventional skin paints, lotions, creams, ointments, aerosols or dusting powders.

The pharmaceutical compositions according to the invention preferably contain the active material at a concentration of 0.1 to 95% by weight, advantageously 0.5 to 40%

For horticultural or agricultural use the compound according to the invention may be formulated for use in any desired way. Generally such formulations will include the compound in association with a suitable carrier or diluent. Such carriers may be liquid or solid and designed to aid the application of the compound either by way of dispersing it where it is to be applied or to provide a formulation which can be made by the user into a dispersible preparation. Thus, for example, the compound of the invention may be formulated as, for example, dusts, powders, granulates; pellets, sprays, smoke and mists, in conventional manner.

In these formulations, the concentration of active material is preferably between 0.01% and 40% by weight.

The compound of the invention may also be of use as a storge preservative in certain materials, for example food, wallpaper paste, paint or petrol, or in beer and wind to prevent undesirable fermentation. In addition the compound may be of use as a seed dressing.

The compound of the invention may be isolated from a fermentation broth prepared by culture of a strain of *Streptomyces clavuligerus*.

Particularly useful strains are *Streptomyces clavuligerus* strain NRRL 3585 and mutants thereof. We have foudn strains NCIB 11261 and NCIB 11260 to be especially useful.

Strain NCIB 11260 is a single colony isolate from strain NRRL 3585 having essentially similar morphology to NRRL 3585 as described in British Patent Specification 1,315,177. Strain NCIB 11261 also has essentially similar morphology to strain NRRL 3585, except that it requires uracil for growth.

As used herein, the term 'mutant' will include any mutant strain which arises either spontaneously or as a result of the action of an external agent, which may be either deliberately applied or otherwise. Mutant strains may be produced by a variety of methods including those outlined in Techniques for the Development of Micro-Organisms by H. I. Adler in "Radiation and Radioisotopes for Industrial Microorganisms", Proceedings of the Symposium, Vienna, 1973, p. 241, International Atomic Energy Authority.

In the preparation of NCIB 11261, we used γ-radiation e.g. of about 80 kilorads. NCIB 11261 has been found to show a requirement of uracil for growth, and the yield of the compound of the invention has been found to be dependent to some extent on the amount of uracil present in the fermentation medium. It is preferred that the level of uracil is not greater than 200 μg/ml of broth, and preferably from 5 to 125 μg/ml.

The production of the compound of formula (I) from *Streptomyces clavuligerus* may be effected by conventional means, i.e. by culturing the *Streptomyces clavuligerus* in the presence of assimilable sources of carbon, nitrogen and mineral salts. Cultivation will preferably be carried out by submerged culture under aerobic conditions.

Assimilable sources of carbon, nitrogen and minerals may be provided by either simple or complex nutrients. Sources of carbon will generally include glucose, starch, glycerol, molasses, dextrin, lactose, sucrose, carboxylic acids, alcohols, for example, methanol, n-paraffins and vegetable oils.

Sources of nitrogen will generally include soyabean meal, corn steep liquors, distillers solubles, yeast extracts, cottonseed meal, peptones, casein, amino acid mixtures, ammonia (gas or solution), ammonium salts or nitrates. Urea and other amides may also be used.

Nutrient mineral salts which may be incorporated into the culture medium include the generally used salts capable of yielding sodium, potassium, ammonium, iron, magnesium, zinc, nickel, cobalt, manganese, vanadium, chromium, calcium, phosphate, sulphate, chloride and carbonate ions.

An antifoam may be present to control excessive foaming and added at intervals as required.

Cultivation of the *Streptomyces clavuligerus* will generally be effected at a temperature of from 20°–37° C., preferably of from 25°–30° C., and will desirably take place with aeration and agitation e.g. by shaking or stirring. The growth medium may initially be inoculated with a small quantity of sporulated suspension of the microorganism but in order to avoid a growth lag a vegetative inoculum of the organism may be prepared by inoculating a small quantity of culture medium with the spore form of the organism, and the vegetative inoculum obtained may be transferred to the fermentation medium, or, more preferably to one or more seed stages where further growth takes place before transfer to the principal fermentation medium.

In a preferred embodiment of the fermentation, a slope of *Streptomyces clavuligerus* NCIB 11261 may be used to inoculate a medium comprising sources of assimilable carbon e.g. sucrose or glycerol, assimilable nitrogen e.g. tryptones, or complex mixtures of assimilable carbon and nitrogen e.g. distiller's solubles and yeast extracts, and nutrient minerals, if necessary with addition or uracil. This medium may be allowed to grow for up to 3 days at from 25°–30° C. with agitation.

The inoculum thus formed may then be used to inoculate (in a quantity of up to about 10%) a nutrient medium containing simple or complex sources of assimilable carbon and nitrogen, uracil and minerals. Growth will desirably be carried out at from 25°–30° C. with agitation and aeration, in one or more stages. The final fermentation stage is normally effected in 2 to 10 days.

The compound of the invention may be isolated from the fermentation medium by conventional isolation techniques. In order to minimise degradation of the compound in solution, the pH during isolation is preferably maintained between 5 and 7. Thus, in general, the fermentation broth will be subjected to filtration, centrifugation and/or other techniques which will remove solid material and provide a clear solution containing the compound of the invention. The compound may then be isolated by a variety of fractionation techniques, for example adsorption-elution, precipitation, solvent extraction etc.

Thus, for example, the fermentation broth from which solid material has been removed may then be applied to one or more materials which may retain either the desired compound or the undesired contaminants. For example, the broth may be treated with an adsorbent carbon on which the compound of the invention is adsorbed. This assists in separating unwanted broth components, particularly salts, from the desired compound.

In general, the clarified broth may be passed through a bed, e.g. in a column, preferably using just sufficient carbon to adsorb all the desired compound usually to a ratio of about 1 part by volume of carbon to 3–10 parts by volume of clarified broth.

The carbon may then be eluted with an aqueous water-miscible solvent, e.g. an alcohol, such as ethanol, or isopropanol, or a ketone such as methyl ethyl ketone, methyl isobutyl ketone or, preferably, acetone, advantageously at a concentration of from 30% to 95% ketone, preferably 50 to 70%. Before elution, the carbon is preferably washed e.g. with water, to remove residual broth components.

In another procedure in which the compound of the invention is retained on adsorbent material, the unclarified or clarified broth may be passed through a suitable resin e.g. a non-ionic resin such as the polystyrene resin XAD-4 (Surface Area 750 m$^2$/gm; Average Pore Diameter 50 Å; Porosity 0.50 to 0.55), sold by Rohm & Haas (UK) Ltd., Croydon, England. The resin will desirably be washed e.g. with water, to remove impurities without eluting the desired compound and the desired compound may then be eluted. In the case of XAD-4 resin, a suitable eluant is an aqueous solution of an alkanol, e.g. methanol, or a ketone e.g. acetone.

Alternatively, the clarified or unclarified fermentation broth or other solution of the compound of the invention in an aqueous medium, which may contain a water-miscible solvent, may be applied to a column which does not retain the compound of the invention but which retains a significant quantity of other material. In one alternative of this process, an aqueous solution of the desired compound e.g. the clarified or unclarified broth or the solution in an aqueous water-miscible solvent (e.g. acetone) obtained as eluate from adsorbent carbon as described above, may be applied to a column of an anion-exchange resin. The resulting solution may then be subjected to fractionation, if required.

The anion exchange resin will generally carry amino groups (weakly basic) or quaternary ammonium groups (strongly basic). The resin may, for example, be a polystyrene, polyacrylic, epoxy-polyamine, phenolic polyamine or cross-linked dextran resin and may be macroreticular or microroreticular. The term 'resin' is used herein for convenience also to include cellulosic derivatives and the above dextran derivatives which are derived from naturally occurring polymers. Typical weakly basic anion exchange resin include Amberlite IRA68 (Microreticular: polyacrylate tertiary amino groups), Amberlite IRA93 (Macroreticular: polystyrene cross-linked with divinylbenzene: tertiary amino groups) all sold by Rohm & Haas (U.K.) Ltd. Typical strongly basic ion exchange resins include Zerolit FF and Zerolit FF (ip) (Sold by Zerolit Co. Ltd.).

In another alternative, the clarified broth may be passed through a non-ionic resin e.g. the polystyrene resin XAD-2 (Surface area 330 m$^2$/gm; Average Pore Diameter 90 Å; Porosity 0.40–0.45) sold by Rohm & Haas (UK) Ltd. which does not retain the desired compound but which will retain several other significant broth components.

In a still further alternative, the desired compound may be extracted into a water-immiscible solvent, e.g. an ester solvent such as ethyl acetate or an alcohol such as butanol. Such extraction may be applied to the clarified or unclarified broth, or to the eluates or effluents from the foregoing adsorption-elution procedures, if necessary after removal of any water-miscible organic solvents which may be present.

To permit extraction into a suitably small volume of water-immiscible solvent it may be desirable to concentrate the solution, e.g. by evaporation under reduced pressure. A high concentration of a salt such as ammonium sulphate assists the extraction.

The desired compound may be further purified by chromatography e.g. on silica or an organic solvent-compatible crosslinked dextran such as Sephadex LH 20 (sold by Pharmacia U.K. Ltd.). The solution of the compound obtained from the previous purification stage may be too dilute for application to the column and may conveniently be concentrated by evaporation under reduced pressure.

The column carrying the desired compound may then be eluted, for example using a solvent of suitable polarity, e.g. in the case of silica columns, ethyl acetate containing a hydrocarbon e.g. hexane or toluene. In the case of Sephadex LH20, a suitable eluant is ethyl acetate alone. In general, the first fractions eluted have been found to contain the desired compound and later fractions have been found to contain predominantly unwanted materials.

Finally, the fractions containing the desired compound may be combined and evaporated to yield the desired compound.

By a suitable combination of the foregoing procedures, the desired compound has been isolated as a pale yellow oil of at least 90% purity. However, in this form the compound is unstable and is best stored in solution in water or organic solvents.

The compound of the invention and methods for its preparation and isolation will now be described in the following non-limiting Examples.

In the Examples which follow the following steam sterilised media were used: In relation to infrared spectra the symbols s, m and w refer to strong, medium and weak intensity respectively.

Medium A

Soya bean meal 5 g/l, yeast extract 5 g/l, tryptone 5 g/l, K$_2$HPO$_4$ 0.2 g/l, glycerol 10 g/l and tap water to 1 liter.

Medium B

Glycerol 35 g/l, citric acid 1.5 g/l, L. asparagine 6.7 g/l, MgSO$_4$.7H$_2$O 0.5 g/l, K$_2$HPO$_4$ 0.21 g/l, KH$_2$PO$_4$ 0.42 g/l, CaCl$_2$ 0.2 g/l, ZnSO$_4$.7H$_2$O 0.05 g/l, FeSO$_4$.7H$_2$O 0.03 g/l, MnSO$_4$.4H$_2$O 0.1 g/l and distilled water to 1 liter.

Medium C

Sucrose 20 g/l, distillers solubles 15 g/l, yeast extract 0.2 g/l, K$_2$HPO$_4$ 0.2 g/l, tryptone 5 g/l, glycerol 10 g/l and tap water to 1 liter.

Medium D

Soya meal (unmilled) 30 g/l, ferric sulphate 0.1 g/l, KH$_2$PO$_4$ 0.1 g/l, soluble starch 47 g/l, silicone antifoam emulsion 0.05 (% v/v) and tap water to 1 liter.

The silica used in column chromatography procedures is woelm silica (activity grade III).

EXAMPLE 1

2-Formyloxymethyl-clavam (a) Fermentation of *Streptomyces clavuligerus* strain

*Streptomyces clavuligerus* strain NCIB 11261 was maintained on malt agar slopes (malt extract 24 g/l; yeast extract 5 g/l; agar 15 g/l; adjusted to pH 7.8) grown for 2 weeks at 28° C. Sterile water (8 ml) was added to each slope and a suspension made. 2 ml portions of this suspension were used to inoculate each of four 250 ml baffled shake flasks containing 50 ml of Medium A containing uracil (100 µg/ml) (pH adjusted to 6.5 with HCl).

The flasks were incubated on a rotary shaker at 220 rev./min with a 5 cm throw, at 26° C. for 24 h. The shake flask contents were bulked and 0.5 ml portions of this inoculum used to inoculate 32×250 ml baffled shake flasks containing the above medium and incubated for 48 h under the previous conditions. 120 ml (3% v/v) portions of this bulked 48 h inoculum were used to inoculate 6×5 liter fermenters each containing 4 liters of Medium B (pH adjusted to 7.0 with NaOH) additionally containing varying levels of uracil.

The uracil concentration and the aeration rate in each fermenter is set out below:

| 5 liter Fermenter No. | Uracil concentration µg/ml | Aeration rate liter/min. |
|---|---|---|
| 1 | 100 | 1.5 |
| 2 | 100 | 3 |
| 3 | 100 | 6 |
| 4 | 50 | 6 |
| 5 | 35 | 6 |
| 6 | 25 | 6 |

The 5 liter fermenters were agitated at 250 rev./min with 2×3½" diameter 4 bladed impellers. The fermentations were maintained at 28° C. for 94 h.

(b) Isolation of 2-formyloxymethyl-clavam

Bulked broth from fermenters 1–6 above (18 l) was centrifuged and the supernatant applied to a column containing XAD-4 resin (bed ht. 130 cm; diam. 2.8 cm).

The resin was washed with water (4 l) and eluted with acetone water (4:1) (c.500 ml). The eluate was evaporated to 100 ml under reduced pressure, the pH adjusted to 6.8 with sodium hydroxide, the solution saturated with ammonium sulphate and extracted with ethyl acetate (4×100 ml). The combined extracts were dried (sodium sulphate), evaporated under reduced pressure and the residue dissolved in a little ethyl acetate. Silica was added and the mixture evaporated under reduced pressure to give a solid which was added to the top of a column containing dry woelm silica (act.grade III bed ht. 50 cm; diam. 2.9 cm). The column was eluted with toluene-ethyl acetate (1:1), 15 ml fractions being taken.

Fractions 4–11 were combined, evaporated under reduced pressure and the residue subjected to chromatography on silica (bed ht. 30 cm; diam. 2.1 cm), with hexane ethyl acetate (2:1) as eluant, 10 ml fractions being collected. Fractions 17–23 were combined and evaporated under reduced pressure to give the formyloxy compound as a pale yellow oil (137 mg). The infrared spectrum of a bromoform solution of the sample is shown in FIG. 1 of the accompanying drawing and has peaks (cm$^{-1}$) at 2915 m, 1784 s, 1730 s, 1462 w, 1406 w, 1392 w, 1346 m, 1282 m, 1066 s, 1034 s, 990 m, 940 w, 926 w and 863 w. A 100 MHz proton nmr spectrum of a solution in deuterochloroform had $\tau$ values as shown in Table 1.

Broth (50 μl) from 5 liter fermenter No: 6 was applied to Merck silica 60 F254 plates, glass-backed, and the plates developed with ethyl acetate, air-dried and overlayed with nutrient agar containing *Saccharomyces carlsbergensis* 1738. The formyloxy compound was found to have an $R_f$ value of 0.89. The formyloxy compound was also detected by quenching of fluorescence under u.v. light (254 nm) after treatment of the developed TLC plate with ammonia vapour.

EXAMPLE 2

2-Formyloxymethyl-clavam (a) Inoculum development

*Streptomyces clavuligerus* NCIB 11260 was stored freeze dried in ampoules. The contents of one ampoule was suspended in sterile distilled water and then added to Medium C adjusted to pH 6.5 with hydrochloric acid in a 250 ml shake flask. The flask was incubated on a rotary shaker at 220 rev/min with a 2" throw at 26° C. for 72 h.

A portion (2 ml) of the 72 h inoculum was used to inoculate each of 4×2 liter florence flasks containing 150 ml of the above medium. The florence flasks were incubated on a rotary shaker at 220 rev/min with a 2" throw at 26° C. for 48 h.

The contents of three of the florence flasks (3×150 ml 3.75 v/v) were used to inoculate 3×5 liter fermenters each containing 4 liters of Medium D (adjusted to pH 6.5 with NaOH/HCl).

These fermenters were agitated with 2×3" diameter 4 bladed impellers at 750 rev/min at 28° C. for 20 h with an air flow of 3 liters/min.

Inoculum (7.5 liters, 5% v/v) from the 5 liter fermenters was used to inoculate 150 liters of the above soya meal medium in a 230 liter stainless steel fermenter. The vessel was agitated with a six bladed 8" impeller at 350 rev/min and aerated at 420 liter/min for 20 h at 28° C.

(b) Fermentation

Broth from the 230 liter fermenter (50 liters, 10% v/v) was used to inoculate 430 liters of Medium D in a 700 liter stainless steel fermenter. The vessel was agitated with a six bladed 10" impeller at 350 rev/min and aerated at 280 liter/min. The fermentation was carried out at 28° C. for 92 h, and was maintained at pH 6.5.

(c) Clarified broth (25 μl) obtained as in (a) and (b) above was applied to Merch silica 60 F254 plates, glass-backed, which were developed with ethyl acetate and air-dried. The plates were then saturated with ammonia vapour and the chromophore produced on reaction with ammonia detected under u.v. light (254 nm). The formyloxy compound was found to have an $R_f$ value of 0.85.

EXAMPLE 3

2-Formyloxymethyl-clavam (a) Inoculum development

*Streptomyces clavuligerus* strain NCIB 11261 was maintained on malt agar slopes (malt extract 2.4%; yeast extract 0.5%; agar 1.5% w/v; pH 7.8) grown for 2 weeks at 28° C. Tween 80 solution (8 ml) was added to the slope and a suspension made. 2 ml portions of this suspension were used to inoculate each of four 250 ml baffled shake flasks containing 50 ml of Medium A containing uracil (100 μg/ml) (pH adjusted to 6.8–7.1).

The flasks were incubated on a rotary shaker at 220 rev./min with a 2" throw, at 28° C. for 48 h. 2 ml portions of this inoculum were used to inoculate identical shake flasks containing the above medium and incubated for 24 h. under the previous conditions. The shake flask contents were bulked and 120 ml portions transferred to 250 ml aspirators. These 120 ml (3% v/v) portions were then used to inoculate 5 liter fermenters each containing 4 L of Medium B containing NaCl (0.1 g/l), antifoam (0.05% v/v) and uracil (35 μg/ml), (pH adjusted to 7.0 with KOH).

The fermenters were agitated at 250 rev./min with 2×3½" diameter 4 bladed impellers. The fermentations were maintained at 28° C. for 24 h. at an aeration rate of 6 l/min.

7.5 l (5% v/v) of this 24 h culture were used to inoculate a 230 liter fermenter containing 150 l of the above medium. The fermentation was maintained at 28° C. for 93 h. at an aeration rate of 5 cu. ft/min and an agitation rate of 250 rev/min.

Further antifoam was added as required throughout the fermentation.

(b) Isolation of 2-formyloxymethyl-clavam (i) Harvest broth (133 l) was adjusted to pH 7.0 with sodium hydroxide and clarified by centrifugation. To the clear supernatant (114 l) ⅓ volume butanol was added, stirred for 30 mins and the phases separated by centrifugation. The aqueous phase (118 l) was re-extracted, separated with butanol as before, and the bulked butanol extracts (76 l) washed with distilled water (40 l).

Distilled water (40 l) was added to the butanol extracts and the azeotrope concentrated to 1 l by means of a pot still and evaporation under reduced pressure. The concentrate was saturated with ammonium sulphate and extracted with 4×½ volume ethyl acetate. The bulked ethyl acetate extracts (1.95 l) were dried with magnesium sulphate, evaporated to 500 ml, dry silica added (Sorbsil M60, 50 g) and evaporated to dryness.

The solid residue was added to the top of a column containing dry silica (Sorbsil M60, 142×3.8 cm) and the silica was eluted with toluene/ethyl acetate (1:1), 25 ml fractions being collected. Fractions 38-73 inclusive were bulked.

(ii) Harvest broth (133 l) prepared as in (a) above was clarified by centrifugation and the supernatant (123 l) evaporated to 22 l on a pot still. The concentrate was adjusted to pH 7.0 with sodium hydroxide, filtered, saturated with ammonium sulphate and extracted with 2×½ volume ethyl acetate. The bulked ethyl acetate extracts (21.5 l) were washed with saturated ammonium sulphate solution (5 l), dried with magnesium sulphate and evaporated to 250 ml under reduced pressure. Sorbsil silica (50 g) was added, the mixture evaporated to dryness and the solid residue added to the top of the column containing dry silica (Sorbsil M60, 138×3.8 cm). The silica was eluted with toluene/ethyl acetate (1:1), 25 ml fractions being taken. Fractions 42 to 60 were bulked.

(iii) The bulked eluates from (i) and (ii) above were combined, evaporated to 15 ml and applied to a column containing LH20 Sephadex (60×6 cm) in ethyl acetate. The Sephadex was eluted with ethyl acetate, 25 ml fractions being collected. Fractions 38-46 were bulked and evaporated to dryness to yield title compound (700 mg) having characteristics similar to those described in Example 1.

EXAMPLE 4

2-Formyloxymethyl-clavam (a) Fermentation of Streptomyces clavuligerus strain

*Streptomyces clavuligerus* strain NCIB 11261 was maintained on malt agar slopes (malt extract 24 g/l; yeast extract 5 g/l; agar 15 g/l; adjusted to pH 7.8) grown for 2 weeks at 28° C.

The slopes were developed for shake flask fermentation with ⅓ of a slope being used to inoculate 50 ml of Medium A (pH adjusted to 6.5) in a 250 ml flask.

This was incubated at 28° C. for 42 h at 220 rev/min on a rotary shaker with a 2" throw. 2 ml of the inoculum was used to inoculate 50 ml of Medium B containing NaCl (0.1 g/l) and uracil (0.01 g/l) (pH adjusted to 7.0 with KOH) in a 250 ml. unbaffled flask. This was kept at 28° C. for 72 h on a rotary shaker with a 5 cm throw at 220 rev/min.

(b) Harvest broth (130 l, pH 5.6) obtained as in (a) above, was clarified by centrifugation and the supernatant (110 l, pH 5.7) adsorbed onto carbon (Pittsburgh CAL, 13 l) in a column. The precipitate at the top of the column was removed, the carbon was washed with water (10 l) and the column was eluted with aqueous acetone (60% v/v, 40 l).

Combined eluates (78 l, pH 6.2) from two lots of harvest broth were applied to a column of IRA 68 resin (chloride cycle, 5 l), the effluent being collected and concentrated under reduced pressure. The pH of the concentrate (20 l) was adjusted to 7.0 with 40% aqueous NaOH solution. The concentrate was saturated with $(NH_4)_2SO_4$ and extracted with ethyl acetate (3×10 l). The bulked extracts were dried (MgSO₄), filtered and concentrated under reduced pressure.

Dry Sorbsil M60 silica (75 g) was added to the concentrated extract (50 ml), and the slurry was dried under reduced pressure. The solid remaining was applied to a column (140×3.5 cm) of dry Sorbsil M60. Elution with ethyl acetate:toluene (1:1 v/v) yielded 2-formyloxymethyl-clavam (fraction between 350 and 2150 ml). A further 2600 ml of ethyl acetate were then passed through the column and collected.

The ethyl acetate collected from the column in (b) above was concentrated under reduced pressure and applied to a column (60×6 cm) of Sephadex LH20 packed in ethyl acetate. The column was eluted with ethyl acetate. Fractions between 1050 ml and 1225 ml yielded further 2-formyloxymethyl-clavam, which was mixed with the fraction obtained from the previous column.

(c) Purification of 2-formyloxy-clavam

The combined eluates from (b) above containing 2-formyloxymethyl-clavam were concentrated under reduced pressure and the concentrate was applied to a column (60×6 cm) of Sephadex LH20 packed in ethyl acetate. The column was eluted with ethyl acetate, fractions between 1025 ml and 1350 ml yielding 2-formyloxymethyl-clavam. A sample of the eluate containing this was dried to an oil ($E_1^1$ after 60 min. in 0.1N NaOH=646).

We claim:

1. A compound of the formula (I)

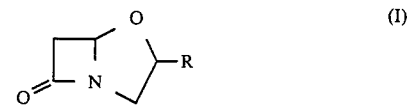

wherein R represents a formyloxymethyl group, said compound in deuterochloroform solution exhibiting the 100 MHz proton n.m.r. τ values as follows: 1.92 (s) (1H), 5.43 (multiplet) (1H), 6.00 (dd, 7 Hz, 11.5 Hz) (1H), 6.70 (dd, 2.5 Hz, 16 Hz) (1H), 4.68 (d, 2.5 Hz) (1H), 5.76 (d, 4 Hz) (2H), 7.20 (dd, 6 Hz, 11.5 Hz) (1H), and 7.19 (d, 16 Hz) (1H) and having a purity of at least 90%.

2. A pharmaceutical antifungal composition comprising an antifungally effective concentration of an antifungal compound of the formula (I)

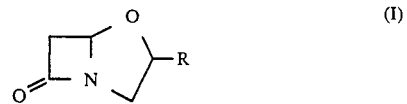

wherein R represents a formyloxymethyl group, said compound in deuterochloroform solution exhibiting the 100 MHz proton n.m.r. τ values as follows: 1.92 (s) (1H), 5.43 (multiplet) (1H), 6.00 (dd. 7 Hz, 11.5 Hz) (1H), 6.70 (dd, 2.5 Hz, 16 Hz) (1H), 4.68 (d, 2.5 Hz) (1H), 5.76 (d, 4 Hz) (2H), 7.20 (dd, 6 Hz, 11.5 Hz) (1H), and 7.19 (d, 16 Hz) (1H) and one or more pharmaceutical carriers or excipients.

3. An antifungal composition for horticultural or agricultural use which comprises an antifungally effective concentration of an antifungal compound of the formula (I)

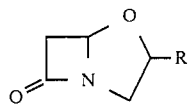

(I)

wherein R represents a formyloxymethyl group, said compound in deuterochloroform solution exhibiting the 100 MHz proton n.m.r. τ values as follows: 1.92 (s) (1H), 5.43 (multiplet) (1H), 6.00 (dd. 7 Hz, 11.5 Hz) (1H), 6.70 (dd, 2.5 Hz, 16 Hz) (1H), 4.68 (d, 2.5 Hz) (1H), 5.76 (d, 4 Hz) (2H), 7.20 (dd, 6 Hz, 11.5 Hz) (1H), and 7.19 (d, 16 Hz) (1H) in association with a carrier or diluent.

4. The composition of claim 3 in the form of a dust, granulate, powder, pellet, spray, smoke or mist.

5. A method of combatting fungi whereby an effective quantity of the composition of claim 2 is administered to a human or animal subject either prophylactically or therapeutically.

6. The pharmaceutical antifungal composition as defined in claim 2 which is a topical composition for external application.

7. The topical composition as defined in claim 6 in the form of a lotion, cream, ointment, aerosol or powder.

8. A method for combatting fungi whereby an effective amount of the topical composition of claim 6 is externally applied to a human or animal subject.

9. The composition of claim 3, wherein the antifungal effective amount comprises 0.1 to 95% by weight of the composition.

10. The composition of claim 9, wherein the amount is from 0.5 to 40%.

11. The composition of claim 4, wherein the antifungal amount is between 0.01% and 40% by weight.

12. A method of treating fungal plant pathogens which comprises applying to plants either prophylactically or therapeutically, an effective amount of the composition of claim 4.

13. The method of claim 12 wherein the antifungal amount of active compound in the composition is between 0.01% and 40% by weight.

* * * * *